(12) United States Patent
Marwah et al.

(10) Patent No.: US 6,384,251 B1
(45) Date of Patent: May 7, 2002

(54) PROCESS FOR EFFECTING ALLYLIC OXIDATION USING DICARBOXYLIC ACID IMIDES AND CHROMIUM REAGENTS

(75) Inventors: Padma Marwah; Henry A. Lardy, both of Madison, WI (US)

(73) Assignee: Humanetics Corporation, Chanhassen, MN (US)

( * ) Notice: Subject to any disclaimer, the term of this patent is extended or adjusted under 35 U.S.C. 154(b) by 0 days.

(21) Appl. No.: 09/423,467

(22) PCT Filed: Mar. 17, 1999

(86) PCT No.: PCT/US99/05609

§ 371 Date: Nov. 8, 1999

§ 102(e) Date: Nov. 8, 1999

(87) PCT Pub. No.: WO99/47485

PCT Pub. Date: Sep. 23, 1999

Related U.S. Application Data
(60) Provisional application No. 60/078,978, filed on Mar. 18, 1998.

(51) Int. Cl.$^7$ .................. C07C 45/00; C07C 69/66; C07J 1/00; C07J 9/00; C07D 317/72
(52) U.S. Cl. .............. 552/542; 552/615; 549/336; 560/174; 568/309; 568/312; 568/317
(58) Field of Search .................. 552/542, 615; 560/174; 568/309, 312, 377; 549/336

(56) References Cited

U.S. PATENT DOCUMENTS

| | | | | |
|---|---|---|---|---|
| 3,914,295 | A | 10/1975 | Rosenthal et al. | 260/524 M |
| 4,263,215 | A | 4/1981 | Hesse et al. | 260/397.2 |
| 4,554,105 | A | 11/1985 | Hesse | 260/397.2 |
| 4,659,829 | A | 4/1987 | Saussine et al. | 546/2 |
| 5,030,739 | A | * 7/1991 | Foricher et al. | 552/542 |
| 5,296,478 | A | 3/1994 | Partridge et al. | 514/178 |
| 5,354,919 | A | 10/1994 | Costantini et al. | 568/432 |
| 5,457,111 | A | 10/1995 | Luly et al. | 514/291 |
| 5,585,371 | A | 12/1996 | Lardy | 514/171 |
| 5,869,709 | A | 2/1999 | Marwah et al. | 552/615 |

FOREIGN PATENT DOCUMENTS

| | | | |
|---|---|---|---|
| WO | WO 95/32215 | 11/1995 | C07J/75/00 |
| WO | wO 96/12810 | 5/1996 | C12N/15/53 |
| WO | WO 97/37664 | 10/1997 | A61K/31/565 |

OTHER PUBLICATIONS

Amann et al., "Stereospecific Synthesis of the Four Epimers of 7,22–Dihydroxycholesterol," *Synthesis*, p. 1002–1005, Nov. 1987.

Barton et al., "Metal Dependence in Gif–type Reactions. The Cu(II)–catalyzed Olefination of Saturated Hydrocarbons by *tert*–Butyl Hydroperoxide," *Tetrahedron Letters*, vol. 34(4), p. 567–570,1993.

"Dictionary of Steroids, Chemical Data, Structure and Bibliographies," *Chapman and Hall*, 1991, p. 267, 509.

Bulman Pate et al., "Oxidation Adjacent to C=C Bonds", *Comprehensive Organic Syntheses*, vol. 7, Pergamon Press, 1991, p. 83–84, 99–117.

Summary of Invention, WO 95/32215, p. 2.

Cheng et al., "Chemistry and Biochemistry of Chinese Druges. Part I. Sterol Derivatives Cytoxic to Hepatoma Cells, Isolated from the Drug," *J. Chem. Research(s* ), p. 217, 1977.

Dauben et al., "Allylic Oxidation of Olevins with Chromium Trioxide–Pyridine Complex," *J. of Org. Chem.*, vol. 34(11), p. 3587–92, Nov. 1969.

Feldberg et al., "Copper–catalysed Oxidation of Hydroxy Compounds by *tert*–Butyl Hydroperoxide under Phase-Transfer Conditions," *J. Chem. Soc., Chem. Commun.*, p. 1807, 1994.

Fullterton et al., "In–Situ Allylic Oxidations with Collins Reagent,"*Synthetic Communications*, vol. 6(3), p. 217–220, 1976.

Kawasaki et al., "Enantioselective Allylic Oxidation Using Biomimetic Tris(oxazolines)–Copper(II) Complex," *Synlett*, (12), p. 1245–46, Dec. 1995.

Kimura et al., "On the Reactions of Cholesteryl Acetate with *tert*–Butyl Hydroperoxide in the Presence of Tris(acetylacetonato)iron(III)," *Chem. Pharm. Bull.*, vol. 27(1), p. 109–12, 1979.

Kimura et al., "The Reactions of Cholesteryl Acetate with Various Hydroperoxides in the Presence of Tris(acetylacetonato)iron(III)," *Chem. Pharm. Bull.*, vol. 28(6), p. 1836–41, 1980.

Kumar et al., "Stereospecific Synthesis of 7Beta–Hydroxycholesterols," *Synthetic Communications*, vol. 17(11), p. 1279–96, 1987.

Marshall et al., "7–Keto Steroids. II. Steroidal 3Beta–and Delta3,5–7–Ones," *J. Am. Chem. Soc.*, vol. 79, p. 6308–13, Dec. 5, 1957.

Muzart, "Synthesis of Unsaturated Carbonyl Compounds via a Chromium Mediated Allylic Oxidatation by 79% Tert.Butylhydroperoxide," *Tetrahedron Letters*, vol. 28(40), p. 4665–68, 1987.

Nagano et al., "Chemistry and Biochemistry of Chinese Drugs, Part II. Hydroxylated Sterols, Cytoxic towards Cancerous Cells: Synthesis and Testing," *J. Chem. Reasearch*(s), p. 218, 1977.

Dodson et al., "Microbiological Transformations. IV. The Oxidation of Dehydroepiandrosterone at C–7," Dec. 5, 1959: 81, 6295–97.

Fieser, "Preparation of Ethylenethioketals," Apr. 5, 1954, 16: 1945–47.

(List continued on next page.)

*Primary Examiner*—Barbara P. Badio

(57) ABSTRACT

A procedure for oxidizing organic compounds having allylic hydrogen atom(s) involving the steps of reactively contacting the organic compound with a combination of an N-hydroxy dicarboxylic acid imide and a chromium-containing oxidant. The reaction can conveniently be conducted under ambient temperature and pressure conditions, and is conveniently conducted in a co-solvent system of water and organic solvent(s).

19 Claims, No Drawings

OTHER PUBLICATIONS

Lardy et al., "Ergosteroids II: Biologcally Active Metabolites and Sythetic Derivatives of Dehydroepiandrosterone," *Steroids*, Mar. 1998: 63(3): 158–65.

Marwah, "Steroidal Allylic Fluorination Using Diethylaminosulfur Trifluoride: A Convenient Method for the Synthesis of 3Beta–acetoxy–7Alpha–and 7Beta–fluoroandrost–5–en–17–one," *Steroids*, Aug. 1996, 61: 454–60.

Singh "Phase–Transfer Catalysed Allylic Oxidation of Hindered Double Bonds in a Rigid Framework by Sodium Periodate," *Indian Journal of Chemistry*, Aug. 1985: 24B:859.

Chidambaram et al., "*tert*–Butyl Hydroperoxide–Pyridinium Dichromate: A Convenient Reagent System Allylic and Benzylic Oxidations," *J. Org. Chem.*, vol. 52, No. 22, 1987, p. 5048–51.

Miller et al., "A Ruthenium Catalyzed Oxidation of Steroidal Alkenes to Enones," *Tetrahedron Letters*, vol. 37, No. 20, 1996, p. 3429–32.

Parish et al., "Allylic Oxidation of Delta5–Steroids with Pyridinium Chlorochromate (PCC) and Pyridinium Dichromate (PDC)," *Synthetic Communications*, vol. 17(10), p. 1227–33, 1987.

Parish et al., "Pyridinium Chlorochromate–Mediated Allylic and benzylic Oxidation," *Synthetic Communications*, vol. 16(11), p. 1371–75, 1986.

Pearson et al., "A New Method for the Oxidation of Alkenes to Enones. An Efficient Synthesis of Delta5–7–Oxo Steroids," *Chem Soc. Perkin Trans. I*, p. 267–73, 1985.

Pearson et al., "Oxidation of Alkenes to Enones Using tert–Butyl Hydroperoxide in the Presence of Chromium Carbonyl Catalysts," *Tetrahedron Letters*, vol. 25(12), p. 1235–38, 1984.

Salmond et al., "Allylic Oxidation with 3,5–Dimethylpyrazole. Chromium Trioxide Complex. Steroidal 5–7–Ketones," *J. Org. Chem.*, vol. 43(10), p. 2057–59, 1978.

Salvador et al., "Copper–Catalysed Allylic Oxidation of 5–Steroids by t–Butyl Hydroperoxide," *Tetrahedron Letters*, vol. 38(1), p. 119–122, 1997.

Sato et al., "Oxygenated Sterols as Inhibitors of Enzymatic Conversion of Dihydrolanosterol into Cholesterol," *Chem. Pharm. Bull.*, vol. 32(8), p. 3305–08, 1984.

Zondervan et al., "Remarkable Reversal of the Non–linear Effect in the Catalytic Enantioselective Allylic Oxidation of Cyclohexene Using Copper Proline Complexes and t–Butyl Hydroperoxide," *Tetrahedron: Asymmetry*, vol. 7(7), p. 1895–98, 1996.

\* cited by examiner

PROCESS FOR EFFECTING ALLYLIC OXIDATION USING DICARBOXYLIC ACID IMIDES AND CHROMIUM REAGENTS

This application is a 371 of PCT/US99/05609 filed Mar. 17, 1999 and claims benefit of provisional application Ser. No. 60/078,978, filed Mar. 18, 1998.

FIELD OF THE INVENTION

The invention relates to the allylic oxidation of organic compounds.

BACKGROUND

Allylic oxidation is a fundamental organic reaction of significant interest to organic chemists practicing in a variety of fields from agricultural products to pharmaceuticals. A variety of procedures are known for oxidizing various organic compounds that possess allylically activated hydrogen(s), but such procedures typically suffer from unsatisfactory yields, tedious workups and/or require the use of expensive reagents.

Allylic oxidation reactions have traditionally been performed with chromium reagents, such as chromium trioxide and sodium/potassium dichromate. While generally effective, such reactions usually require a large excess of the reagent under harsh conditions (e.g., a large volume of aqueous acetic acid, anhydrous acetic acid (Fieser's Reagent) or concentrated or dilute sulfuric acid). Chromium trioxide pyridine complex allows the oxidation to be carried out at ambient temperature, but requires the use of a large excess of the reagent (~20 equiv.) and is highly hygroscopic, making the reagent unattractive for large scale production.

Pyridinium chlorochromate (PCC) and pyridinium dichromate have more or less become ubiquitous for chromate based oxidations as they are generally effective and can be prepared by a procedure significantly less hazardous than that required to prepare the chromium trioxide-pyridine complex. However, these reagents also tend to require a large excess (~20 equiv.) of the reagent. The use of tert-butyl hydroperoxide in combination with a chromium reagent affords allylic oxidation under relatively mild processing conditions, but often requires the use of an undesirable organic solvent such as benzene.

A further drawback associated with the aforementioned procedures is the incomplete nature of the conversion, requiring the implementation of expensive techniques, such as chromatography, to remove unreacted starting material and obtain a product of sufficient purity.

Hence, a continuing need exists for a simple, efficient, safe and cost effective procedure for selectively effecting the allylic oxidation of organic compounds, particularly Δ5-steroids, suitable for use on a commercial scale.

SUMMARY OF THE INVENTION

We have discovered a simple, efficient, safe, and cost effective procedure for oxidizing organic compounds having allylic hydrogen atom(s). The procedure involves reactively contacting an organic compound having an allylic hydrogen atom(s) with a combination of a chromium compound and an N-hydroxy dicarboxylic acid imide under conditions sufficient to effect oxidation of the allylic hydrogen(s) on the organic compound.

The successful incorporation of an N-hydroxy imide of a suitable dicarboxylic acid with a chromium oxidant allows the reaction to be conveniently conducted at ambient or near ambient temperature and normal pressure using conventional, relatively safe organic solvents.

DETAILED DESCRIPTION OF THE INVENTION INCLUDING A BEST MODE

Definitions

As utilized herein, including the claims, the term "allylic compound" references an organic compound having at least one allylic hydrogen atom.

As utilized herein, including the claims, the term "allylic oxidation" means oxidation of an allylic compound by replacing at least one allylic hydrogen(s) with oxygen or an oxygen-containing group.

As utilized herein, including the claims, the term "reactants" collectively references allylic substrates, N-hydroxy dicarboxylic acid imides and chromium-containing compounds. Solvents, including both aqueous and organic solvents, are specifically excluded from the definition of reactants.

Process

The present process is extremely useful both in terms of yield and operational simplicity. This is particularly true for the allylic substrates of Δ5-steroids and benzylic compounds. Excellent yields are obtained with low molar ratios of the reactants under ambient or near ambient conditions. Of particular interest is the discovery that the process achieves the desired allylic oxidation with a near total absence of any competitive side reactions.

The process involves reactively contacting an allylic compound with a combination of N-hydroxy dicarboxylic acid imide and a chromium-containing oxidant(s), under conditions sufficient to effect oxidation of the allylic hydrogen atom(s) on the organic compound. For example, an allylic compound can be dissolved in a suitable organic solvent and a mixture of the N-hydroxy dicarboxylic acid imide and chromium-containing oxidant(s) added. Water may optionally be incorporated into the reaction mixture in a suitable amount.

Constituents

Allylic Compounds

Allylic compounds are any organic compound incorporating the structure $—RC^1=C^2H—C^3H_n—$ within the molecule, wherein n is 1, 2 or 3. Hydrogen atoms attached to the $C^1$ and $C^2$ carbon atoms are referenced as vinylic hydrogen. Hydrogen atoms attached to the $C^3$ carbon atom are referenced as allylic hydrogen. The process of this invention selectively oxidizes allylic hydrogen atoms over vinylic hydrogen atoms. Exemplary allylic compounds include specifically, but not exclusively, (i) aliphatic vinylic compound such as methyl oleate, (ii) aromatic benzylic compounds such as fluorene and diphenyl methane, (iii) isoprenoids, such as carotenoids, terpenes, sesquiterpenes and vitamins, and (iv) steroids and sterols, such as androstenes, cholesterol, estraenes, pregnenes and derivatives thereof such as esters, esters, and ketals of these compounds.

Of particular commercial interest is the allylic oxidation of steroids, particularly Δ5 steroids such as dehydroepiandrosterone and derivatives of dehydroepiandrosterone, because such steroids possess pharmacological activity and can be conveniently and effectively allylically oxidized in excellent yields by the process of this invention.

Cooxidants

The procedure utilizes a cooxidant system of N-hydroxy dicarboxylic acid imide and a chromium-containing oxidant.

A cooxidant system of a N-hydroxy dicarboxylic acid imide and chromium-containing oxidant is used to allylically oxidize the allylic compound. Experimentation has shown the specific combination of N-hydroxy dicarboxylic acid imide and chromium-containing oxidant generally provides a superior yield and/or superior quality of allylically oxidized product under mild reaction conditions.

N-hydroxy Dicarboxylic Acid Imide

The N-hydroxy dicarboxylic acid imide includes those formed from dicarboxylic acids which can form cyclic imides in accordance with the general formula:

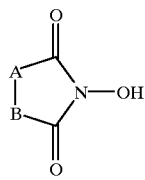

wherein X-Y stands for saturated or unsaturated aliphatic hydrocarbon residue, aromatic hydrocarbon residue or a group derived from one of the groups.

Preferred examples of the imide include N-hydroxy succinimide, N-hydroxy-phthalimide, N-hydroxy imides of naphthalene dicarboxylic acids, and derivatives thereof.

Chromium-containing Oxidants

A number of chromium-containing oxidants are known in the art. Preferred examples of chromium-containing oxidants include sodium dichromate monohydrate (SDC), chromium trioxide (CTO), pyridinium chlorochromate (PCC), pyridinium dichromate (PDC), and chromium perchlorate hexahydrate (CPC).

Both the N-hydroxy dicarboxylic acid imide and chromium-containing oxidants are available from a number of chemical suppliers as an aqueous solution. Since the reaction mixture may include small amounts of water, the oxidants can generally be used as obtained.

Generally, the concentrations of N-hydroxy dicarboxylic acid imide (Imide) and chromium-containing oxidant (Chromium) set forth in Table One below are effective for allylically oxidizing an allylic compound.

TABLE ONE

| | CONCENTRATION | | |
|---|---|---|---|
| OXIDANT | GENERALLY (Mole/Eq) | PREFERRED (Mole/Eq) | MOST PREFERRED (Mole/Eq) |
| Imide | 0.5–1.5 | 0.7–1.2 | 1 |
| Chromium | 0.5–3 | 0.7–2.5 | 1–2 |

Concentrations of less than about 0.5 mole equivalent of chromium-containing oxidant and less than about 0.5 mole equivalents of N-hydroxy dicarboxylic acid imide significantly slows the reaction, while greater than about 3 mole equivalents of chromium-containing oxidant, and greater than about 1.5 mole equivalents of N-hydroxy dicarboxylic acid imide increases the cost of the process without producing a corresponding increase in any beneficial property or characteristic of the process or resultant product(s).

Organic Solvent(s)

The organic reactants (i.e., allylic compound and N-hydroxy dicarboxylic acid imide) can be conveniently dissolved in suitable organic solvent(s), with selection of the solvent dependent upon the specific allylic compound and N-hydroxy dicarboxylic acid imide used.

The solvent should be selected based primarily upon cost and ease of handling, and as well as its ability to dissolve the organic reactants and facilitate reactive contact between the chromium-containing oxidant(s) and the organic reactants. Conventional organic solvents generally suitable for use in the process include specifically, but not exclusively: aliphatic ketones like acetone, aliphatic alkyl nitrites like acetonitrile, and lower alcohols like t-butanol. Such solvents may be used alone or in combination with small amounts of an organic base(s) like pyridine.

Processing Parameters and Procedures

Reaction Time

While dependent upon a number of variables, including the specific allylic compound being oxidized, the specific cooxidants being used and the concentration of reactants within the reaction mixture, the reaction can typically be conducted in about 20 to about 48 hours.

Reaction Temperature

The reaction is preferably conducted at ambient or near ambient temperatures (i.e., temperatures between about 20° to 35° C.).

Mixing

The reaction mixture should be continuously and vigorously stirred in order to promote contact between the reactants and thereby speed-up the reaction and enhance the yield and/or quality of the desired allylically oxidized organic compound.

Solvent Dilution Factor

As with any solvent-based reaction, the wt % solids should be retained between an upper solubility limiting percentage and a lower reaction rate limiting percentage. As the upper limiting wt % of solids is reached, the viscosity of the resultant reaction mixture increases to such an extent that the necessary molecular interaction of the reactants are limited (e.g., the reaction mixture cannot be effectively mixed, with a resultant loss in yield and/or increased reaction time). Conversely, as the lower limiting wt % of solids is reached, the reaction time begins to increase dramatically due to the reduced opportunity for the reactants to encounter one another within the reaction time. Such low concentrations of solids also results in increased expense due to the excessive amounts of solvent used per unit of reaction product obtained.

While the preferred wt % of solids in the reaction mixtures of this invention depend upon a number of variables, including the specific solvent(s) used and the specific reactants employed, a solids wt % of between about 5 to 20 wt % has been found to be generally acceptable for producing a high yield of good quality product at a reasonable rate of reaction.

Separation and Purification Techniques

Upon completion of the oxidation reaction, the allylically oxidized organic compound can be separated from the solvent system, as well as any unused reactants and any byproducts, by any of a variety of separation techniques known to those skilled in the art, including: (i) dilution, (ii) filtration, (iii) extraction, (iv) evaporation, (v) distillation, (vi) decantation, (vii) crystallization/recrystallization, and/or (viii) chromatography.

The N-hydroxy dicarboxylic acid imide can be substantially recovered from the reaction mixture (i.e., about 80% recovery) simply by (i) filtering the reaction mixture through a bed of celite or similar material (ii) concentrating the organic layer, and (iii) treating the organic layer with toluene, dichloromethane or ethyl acetate.

Any chromium-containing substance(s) can be conveniently removed from the system by (i) evaporating the reaction solvent under vacuum, (ii) re-dissolving the crude solid in dichloromethane or ethyl acetate, and then (iii) filtering the reaction mixture through a bed of celite or similar material.

The isolated allylically oxidized product can be further purified by various known techniques, such as washing the isolated product with a solvent effective for selectively dissolving any remaining contaminants without dissolving appreciable quantities of the product, such as water and/or suitable organic solvents like dichloromethane, ethyl acetate, etc.

EXAMPLES

Standard Protocol

An allylic substrate (10 mmole) and a N-hydroxy dicarboxylic acid imide (10 mmole) are dissolved in an organic solvent (100 ml) with or without added water. A solid chromium-containing oxidant(s) (10–30 mmole) is added to the solution at room temperature under constant agitation with a magnetic stirrer for a specified time period. The resultant reaction mixture is evaporated to dryness, taken up in a water immiscible organic solvent and filtered through celite. The filtered organic solvent is then washed with an aqueous saturated solution of $NaHCO_3$, water and brine. The organic solvent phase, usually dichloromethane or ethyl acetate, is treated with bentonite, filtered, and evaporated to dryness to yield an allylically oxidized product.

The following examples serve to illustrate the allylic oxidation of aliphatic vinylic compounds, aromatic benzylic compounds, isoprenoid compounds, and steroid compounds employing the cooxidants N-hydroxy dicarboxylic acid imide and chromium-containing oxidant.

EXAMPLES 1–10

Oxidation with Sodium Dichromate and N-Hydroxy Phthalimide

EXAMPLE 1

Oxidation of 3β-Acetoxyandrost-5-en-17-one (DHEAAc) to 3β-Acetoxyandrost-5-ene-7,17-dione (7-Oxo-DHEAAc)

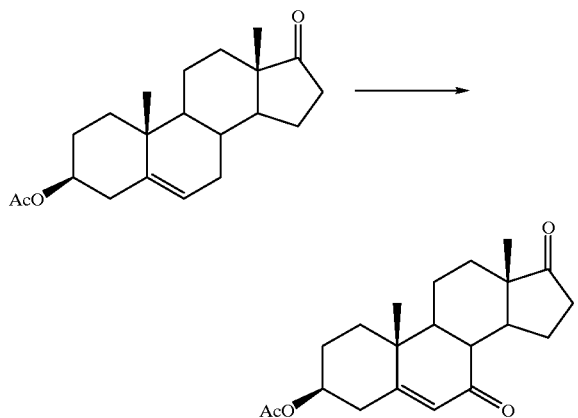

Oxidation

3β-Acetoxyandrost-5-en-17-one (DHEAAc) (3.3 g, 0.01 mol) and N-hydroxy phthalimide (3.3 g, 0.02 mol) were dissolved in acetone (100 ml). The mixture was stirred vigorously at room temperature and solid sodium dichromate monohydrate (1.5 g, 0.005 mol) was added. After 10 and 20 hours of continuous stirring, additional amounts of solid sodium dichromate monohydrate (0.75 g, 0.0025 mol) were added at each time interval, and the reaction mixture stirred continuously until the reaction had run to completion (60 hours).

Separation

Acetone was removed from the reaction mixture under reduced pressure and the residue taken up in dichloromethane (50 ml) and filtered through a bed of celite, with the filter cake washed twice with dichloromethane. The combined organic filtrate was washed with saturated sodium bicarbonate solution and water. The washed filtrate was mixed with bentonite (10.0 g), filtered, and evaporated to dryness. The resulting solid residue was dissolved in methanol (40 ml) and cooled to produce 2.8 g (81.4%) of white solid 3β-Acetoxyandrost-5-en-7,17-dione (7-oxo-DHEAAc) having a melting point of 185–186° C.

EXAMPLE 2

(Oxidation of 3β-Acetoxyandrost-5-en-17-one (DHEAAc) to 3β-Acetoxyandrost-5-ene-7,17-dione (7-Oxo-DHEAAc)

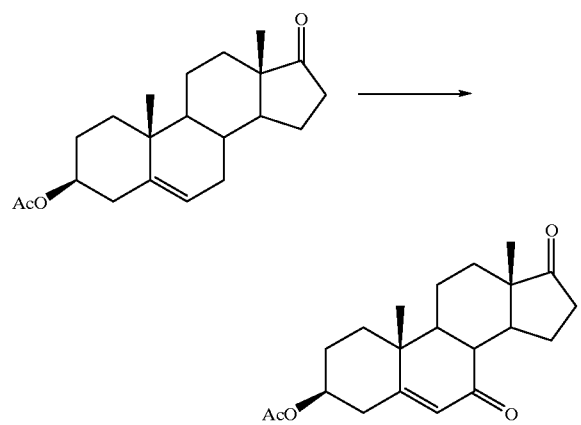

Oxidation

3β-Acetoxyandrost-5-en-17-one (DHEAAc) (3.3 g, 0.01 mol) and N-hydroxy phthalimide (1.8 g, 0.011 mol) were dissolved in acetone (100 ml). The mixture was stirred vigorously at room temperature and solid sodium dichromate monohydrate (1.5 g, 0.005 mol) and chromium perchlorate hexahydrate (1.0 g, 0.002 mol) were added. After 10 and 20 hours of continuous stirring at room temperature, additional amounts of solid sodium dichromate monohydrate (1.5 g, 0.005 mol) and chromium perchlorate hexahydrate (1.0 g, 0.002 mol) were added at each time interval, and the reaction mixture stirred continuously until the reaction had run to completion (36 hours).

Separation

Acetone was removed from the reaction mixture under reduced pressure and the residue taken up in dichloromethane (50 ml), and filtered through a bed of celite, with the filter cake washed twice with dichloromethane. The combined organic filtrate was washed twice with saturated sodium bicarbonate solution and water. The washed filtrate was mixed with bentonite (10.0 g), filtered, and solvent removed by distillation to form a crude material which weighed 3.1 g having a melting point of 182–185° C. The solid was recrystallized from methanol to yield 2.95 g (85.8%) of white crystalline 3β-Acetoxyandrost-5-en-7,17-dione (7-oxo-DHEAAc) having a melting point of 185–187° C.

EXAMPLE 3

(Oxidation of 3β-Acetoxyandrost-5-en-17-one (DHEAAc) to 3β-Acetoxyandrost-5-ene-7,17-dione (7-Oxo-DHEAAc))

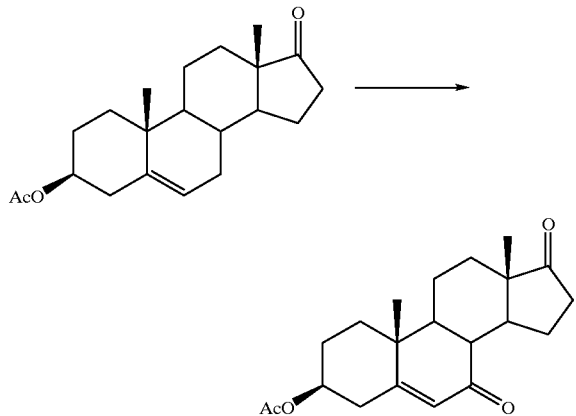

Oxidation

3β-Acetoxyandrost-5-en-17-one (DHEAAc) (0.33 g, 0.001 mol) and N-hydroxy phthalimide (0.2 g, 0.0012 mol) were dissolved in acetone (10 ml) containing 0.2 ml of glacial acetic acid. The mixture was stirred vigorously at room temperature and solid sodium dichromate monohydrate (0.15 g, 0.0005 mol) was added. After 10 hours of continuous stirring at room temperature, an additional amount of solid sodium dichromate monohydrate (0.15 g, 0.0005 mol) was added, and the reaction mixture stirred continuously until the reaction had run to completion (24 hours).

Separation

The reaction mixture was diluted with dichloromethane, then washed with water, saturated sodium bicarbonate solution and water. The washed organic layer was dried over magnesium sulfate and the solvent removed by distillation to form a crude material. The solid was recrystallized from methanol to yield 0.26 g (75.6%) of white crystalline 3β-Acetoxyandrost-5-en-7,17-dione (7-oxo-DHEAAc) having a melting point of 184–186° C.

EXAMPLE 4

(Oxidation of 3β-Acetoxyandrost-5-en-17-one (DHEAAc) to 3β-Acetoxyandrost-5-ene-7,17-dione (7-Oxo-DHEAAc))

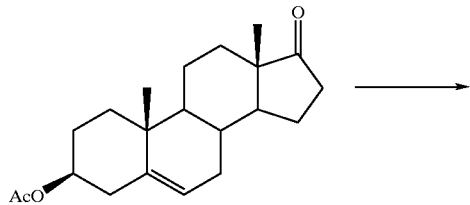

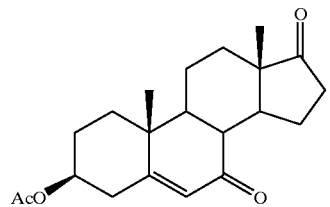

Oxidation

3β-Acetoxyandrost-5-en-17-one (DHEAAc) (3.3 g, 0.01 mol) and N-hydroxy phthalimide (1.8 g, 0.011 mol) were dissolved in acetonitrile (90 ml) and water (10 ml). The mixture was stirred vigorously at room temperature and solid sodium dichromate monohydrate (1.5 g, 0.005 mol) and chromium perchlorate hexahydrate (1.0 g, 0.002 mol) were added. After 10 and 20 hours of continuous stirring at room temperature, additional amounts of solid sodium dichromate monohydrate (1.5 g, 0.005 mol) and chromium perchlorate hexahydrate (1.0 g, 0.002 mol) were added at each time interval, and the reaction mixture stirred continuously until the reaction had run to completion (48 hours).

Separation

Acetonitrile was removed under reduced pressure and the crude product taken up in dichloromethane, and filtered through a bed of celite. The combined organic filtrate was washed with water, saturated sodium bicarbonate solution and water. The washed organic layer was dried over magnesium sulfate and solvent removed by distillation to form a crude material. The solid was stirred with diethyl ether, cooled and filtered to yield 3.2 g (93.0%) of white crystalline 3-Acetoxyandrost-5-en-7,17-dione (7-oxo-DHEAAc) having a melting point of 185–186° C.

EXAMPLE 5

Oxidation of 3β-acetoxy-7,17-ethylenedioxyandrost-5-ene to 3β-acetoxy-17,17-ethylenedioxyandrost-5-en-7-one

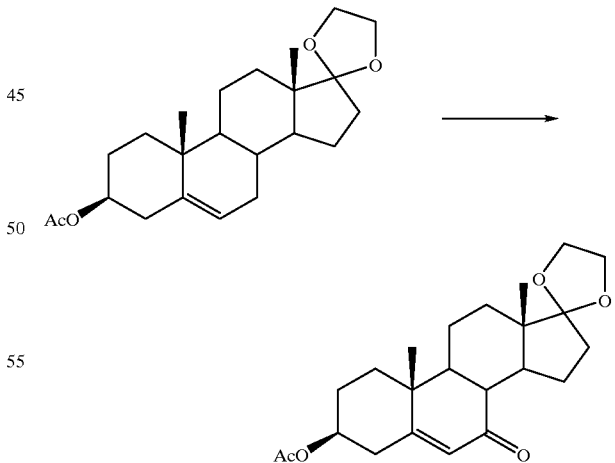

Oxidation

3β-Acetoxy-17,17-ethylenedioxyandrost-5-ene (0.37 gram, 0.001 mol) and N-hydroxy phthalimide (0.36 g, 0.0022 mol) were dissolved in acetone (20 ml) containing 0.5 ml of pyridine. The mixture was stirred vigorously at room temperature and solid sodium dichromate monohydrate (0.15 g, 0.0005 mol) was added. After 10 and 20 hours of continuous stirring, additional amounts of solid sodium dichromate monohydrate (0.15 g, 0.0005 mol) were added at each time interval, and the reaction mixture stirred continuously until the reaction had run to completion (48 hours).

Separation

The reaction mixture was diluted with dichloromethane and filtered in a bed of celite, with the organic filtrate washed with water, saturated sodium bicarbonate solution and water. The washed organic layer was dried over magnesium sulfate and the solvent removed by distillation to form a crude material.

Purification and Characterization

The crude solid was chromatographed on silica gel using ethyl acetate-petroleum ether (3:7) as eluent. The purified 3β-acetoxy-17,17-ethylenedioxyandrost-5-en-7-one was recrystallized from methanol to yield 0.32 gram (82.5%) of pure crystalline 3β-acetoxy-17,17-ethylenedioxyandrost-5-en-7-one as white needles having a melting point of 182–183° C. (melting point for compound listed in the literature as 175–177° C. in Fieser L. R.-JACS 76, 1945, (1954)).

EXAMPLE 6

(Oxidation of 3β-hydroxy-androst-5-en-17-one (DHEA) to 3β-hydroxy-androst-5-ene-7,17-dione (7-Oxo-DHEA)

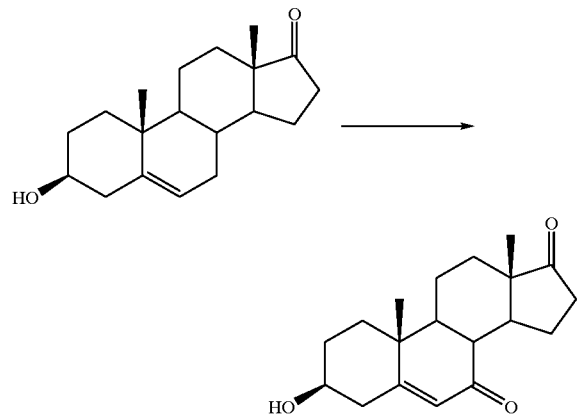

Oxidation

3β-hydroxy-androst-5-en-17-one (DHEA) (2.88 grams, 0.01 mol) and N-hydroxy phthalimide (1.8 g, 0.011mol) were dissolved in acetone (100 ml). The mixture was stirred vigorously at room temperature and solid sodium dichromate monohydrate (1.5 g, 0.005 mol) and chromium perchlorate hexahydrate (0.5 g, 0.001 mol) were added. After 10 and 20 hours of continuous stirring at room temperature, additional amounts of solid sodium dichromate monohydrate (1.5 g, 0.005 mol) and chromium perchlorate hexahydrate (0.5 g, 0.001 mol) were added at each time interval, and the reaction mixture stirred continuously until the reaction had run to completion (48 hours).

Separation

Acetone was removed from the reaction mixture under reduced pressure and the residue taken up in dichloromethane (50 ml) and filtered through a bed of celite, with the cake washed twice with dichloromethane. The combined organic filtrate was washed twice with saturated sodium bicarbonate solution and water. The washed filtrate was mixed with bentonite (10.0 g), filtered, and solvent removed by distillation to form a crude material. The crude product was dissolved in methanol by heating, and cooled to produce 1.32 grams of 7-oxo-DHEA, having a melting point of 234–236° C.

Secondary Recovery

The mother liquor solvent was removed by a rotary evaporator and the resulting residue chromatographed on a short column of silica gel (70–230) using hexane-ethyl acetate (60:40) as eluent. The first fraction gave the starting DHEA (0.9 g, 31.25% recovered) followed by an additional amount (0.2 gram) of 7-oxo-DHEA.

Crystallization

The combined 7-oxo-DHEA was recrystallized from methanol to provide a purified product having a melting point of 239–241 ° C.

Yield

Total combined yield of 7-oxo-DHEA was 1.52 gram (74.25% based on 68.75% conversion).

EXAMPLE 7

Oxidation of 3β-acetoxycholest-5-ene (CholesterylAc) to 3β-acetoxycholest-5-en-7-one (7-Oxo-CholesterylAc)

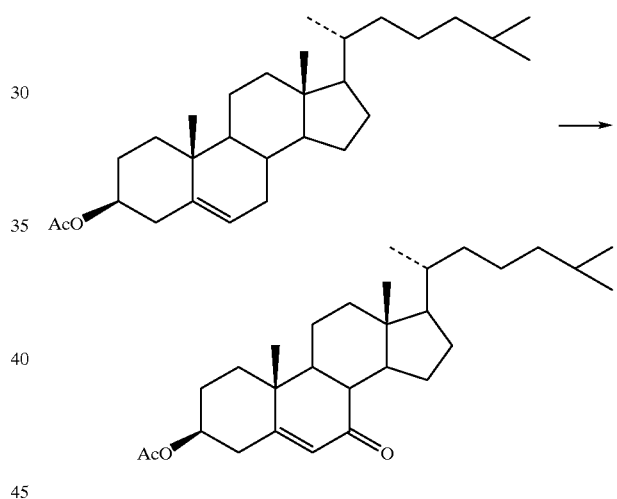

Oxidation

Cholesteryl acetate (2.14 grams, 0.005 mol) and N-hydroxy phthalimide (1.0 g, 0.006 mol) were dissolved in acetone (70 ml). The mixture was stirred vigorously at room temperature and solid sodium dichromate monohydrate (0.60 g, 0.002 mol) was added. After 10 and 20 hours of continuous stirring, additional amounts of solid sodium dichromate monohydrate (0.60 g, 0.002 mol) were added at each time interval, and the reaction mixture stirred continuously until the reaction had run to completion (36 hours).

Separation

The reaction mixture was diluted with dichloromethane and water, and filtered through a bed of celite. The dichloromethane layer was separated and then washed with water, saturated sodium bicarbonate solution and water. The organic solvent was evaporated under reduced pressure to yield a crude product which was recrystallized from methanol. The crystalline material was collected under suction, washed with cold methanol, and dried to yield 1.95 grams (88%) of 7-oxo-cholesteryl acetate having a melting point of 155–156° C.

EXAMPLE 8

Oxidation of Fluorene to Fluorenone

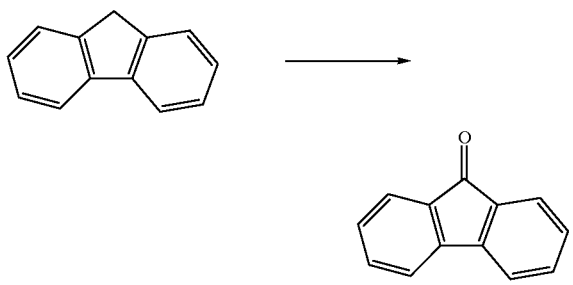

Oxidation

Fluorene (1.66 grams, 0.01 mol) and N-hydroxy phthalimide (1.8 g, 0.011 mol) were dissolved in acetone (100 ml). The mixture was stirred vigorously at room temperature and solid sodium dichromate monohydrate (1.38 g, 0.0046 mol) and chromium perchlorate hexahydrate (1.17 g, 0.0025 mol) were added. After 10 and 20 hours of continuous stirring at room temperature, additional amounts of solid sodium dichromate monohydrate (1.38 g, 0.0046 mol) and chromium perchlorate hexahydrate (1.17 g, 0.0025 mol) were added at each time interval. After 30 hours of continuous stirring at room temperature an additional amount of solid sodium dichromate monohydrate (1.38 g, 0.0046 mol) was added and the reaction mixture stirred continuously until the reaction had run to completion (48 hours).

Separation

Solvent was removed under vacuum and dichloromethane (50 ml) added to the residue. The organic layer was filtered through a bed of celite and the filter cake washed three times with dichloromethane. The combined organic filtrate was washed with water, saturated sodium bicarbonate solution and water. The washed filtrate was dried and the solvent distilled to yield fluorenone. The crude fluorenone was recrystallized from methanol to yield fluorenone (1.64 grams) having a melting point of 82–84° C.

Yield

Total yield of fluorenone was 1.64 grams (91.0%).

EXAMPLE 9

Oxidation of R(+)α-Pinene to R(+)α-Verbenone

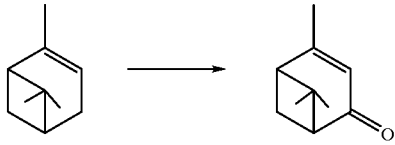

Oxidation

R(+)α-pinene (1.56 grams, 0.012 mol) and N-hydroxy phthalimide (2.0 g, 0.012 mol) were dissolved in acetone (70 ml). The mixture was stirred vigorously at room temperature and solid sodium dichromate monohydrate (1.5 g, 0.005 mol) was added. After 10 and 20 hours of continuous stirring, additional amounts of solid sodium dichromate monohydrate (1.5 g, 0.005 mol) were added at each time interval, and the reaction mixture stirred continuously until the reaction had run to completion (44 hours).

Separation

Acetone was removed from the reaction mixture by evaporation and the residue diluted with dichloromethane and filtered through a bed of celite, with the filter cake washed with dichloromethane. The combined filtrate was washed twice with saturated sodium bicarbonate solution and water, and the solvent evaporated to form a crude product.

The crude product was chromatographed on a silica gel column (70–230). The product was eluted with ethyl acetate (3–5% (v/v)) in hexane to yield pure R(+)α-verbenone (0.82 grams).

Yield

Total yield of purified R(+)α-verbenone was 0.82 grams (47.4%).

EXAMPLE 10

Oxidation of Methyl 9-octadecenoate to a Mixture of the Isomeric Methyl 8-oxo-9-octadecenoate and Methyl 11-oxo-9-octadecenoate

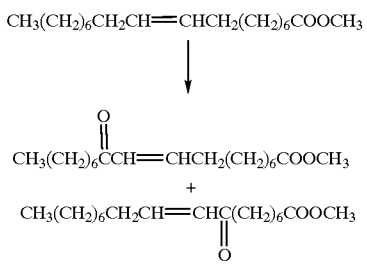

Oxidation

Methyl oleate (1.1 grams, 0.0029 mol) and N-hydroxy phthalimide (0.6 g, 0.0037 mol) were dissolved in acetone (30 ml). The resultant solution was stirred vigorously at room temperature and solid sodium dichromate monohydrate (0.5 g, 0.0017 mol) and chromium perchlorate hexahydrate (0.33 g, 0.0007 mol) were added. After 10 and 20 hours of continuous stirring at room temperature, additional amounts of solid sodium dichromate monohydrate (0.5 g, 0.0017 mol) and chromium perchlorate hexahydrate (0.33 g, 0.0007 mol) were added at each time interval, and the reaction mixture stirred continuously for 48 hours.

Separation

Acetone was removed from the reaction mixture by evaporation, the residue diluted with dichloromethane and filtered through a bed of celite, with the filter cake washed with dichloromethane. The combined filtrate was washed twice with saturated sodium bicarbonate solution and water, and the solvent evaporated to form a crude oily residue. The resulting oily residue was chromatographed on a column of silica gel (70–230) and eluted with ethyl acetate (0 to 5% (v/v)) in petroleum ether. The fractions eluted with pure petroleum ether were combined and distilled to yield 0.22 gram (20.0%) of unreacted methyl oleate. The fractions eluted with 5% (v/v) ethyl acetate in petroleum ether were combined and evaporated to yield 0.435 gram (48.3%) of a white oil.

The white oil was found to be a 1:1 mixture of methyl 11-oxo-9-octadecenoate and methyl 8-oxo-9-octadecenoate as shown by 1H NMR and TLC (TLC plates were impregnated with boric acid and silver nitrate, dried and activated at 120° C. for 4 hours before use, and a mixture of 10% (v/v) ether in petroleum ether used as a mobile phase).

Yield

Total yield of product was 0.435 gram (48.3% based upon 80% conversion).

EXAMPLES 11–16

Oxidation with Chromium Trioxide and N-Hydroxy Phthalimide

EXAMPLE 11

(Oxidation of 3β-Acetoxyandrost-5-en-17-one (DHEAAc) to 3β-Acetoxyandrost-5-ene-7,17-dione (7-Oxo-DHEAAc)

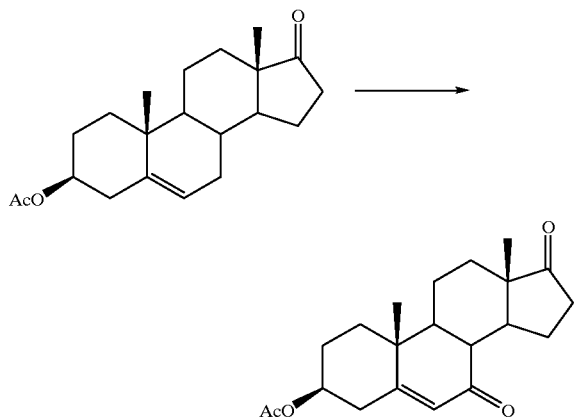

Oxidation

3β-Acetoxyandrost-5-en-17-one (DHEAAc) (0.33 g, 0.001 mol) and N-hydroxy phthalimide (0.18 g, 0.0011 mol) were dissolved in acetonitrile (9 ml) and water (1 ml). The mixture was stirred vigorously at room temperature and solid chromium trioxide (0.1 g, 0.001 mol) was added. After 3 hours of continuous stirring at room temperature, an additional amount of solid chromium trioxide (0.1 g, 0.001 mol) was added, and the reaction mixture stirred continuously until the reaction had run to completion (20 hours).

Separation

The reaction mixture was diluted with dichloromethane, then washed with water, saturated sodium bicarbonate solution and water. The washed organic layer was treated with bentonite, filtered, and solvent removed by distillation to form a crude material. The solid crude material was triturated with diethyl ether to yield 0.285 g (82.8%) of white crystalline 3β-Acetoxyandrost-5-en-7,17-dione (7-oxo-DHEAAc) having a melting point of 185–186° C.

EXAMPLE 12

(Oxidation of 3β-Acetoxyandrost-5-en-17-one (DHEAAc) to 3β-Acetoxyandrost-5-ene-7,17-dione (7-Oxo-DHEAAc)

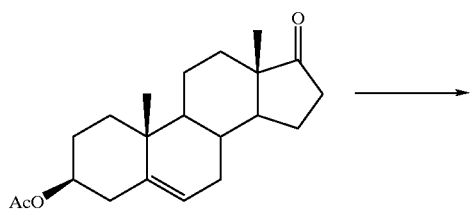

-continued

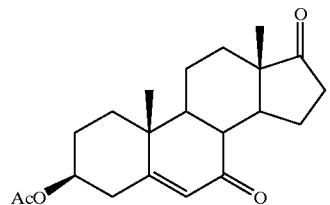

Oxidation

3β-Acetoxyandrost-5-en-17-one (DHEAAc) (0.33 g, 0.001 mol) and N-hydroxy phthalimide (0.18 g, 0.0011 mol) were dissolved in t-butanol (9 ml) and water (1 ml). The mixture was stirred vigorously at room temperature and solid chromium trioxide (0.2 g, 0.002 mol) was added. The reaction mixture was thereafter stirred continuously until the reaction had run to completion (20 hours).

Separation

The reaction mixture was poured into water and the aqueous solution extracted with dichloromethane. The dichloromethane extract was washed with water, saturated sodium bicarbonate solution and water. The washed organic layer was treated with bentonite, filtered, and solvent removed by distillation to form a crude material. The solid crude material was triturated with diethyl ether to yield 0.28 g (81.4%) of white crystalline 3β-Acetoxyandrost-5-en-7,17-dione (7-oxo-DHEAAc) having a melting point of 185–186° C.

EXAMPLE 13

(Oxidation of 3β-Acetoxyandrost-5-en-17-one (DHEAAc) to 3β-Acetoxyandrost-5-ene-7,17-dione (7-Oxo-DHEAAc)

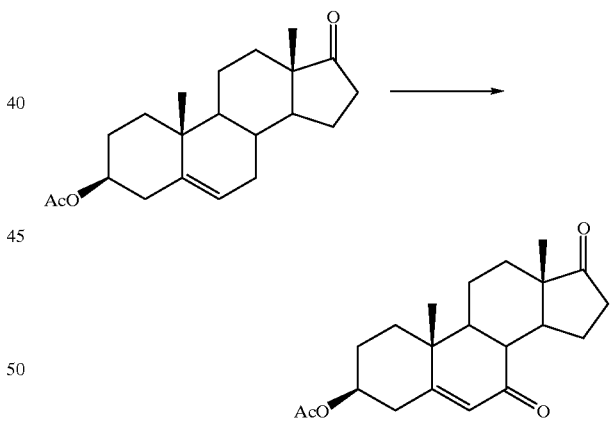

Oxidation

3β-Acetoxyandrost-5-en-17-one (DHEAAc) (3.3 g, 0.01 mol) and N-hydroxy phthalimide (1.8 g, 0.011 mol) were dissolved in acetone (45 ml) and water (5 ml). The mixture was stirred vigorously at room temperature and solid chromium trioxide (1.0 g, 0.01 mol) was added over one hour. After 3 hours of continuous stirring at room temperature, an additional amount of solid chromium trioxide (1.0 g, 0.01 mol) was added, and the reaction mixture stirred continuously until the reaction had run to completion (20 hours).

Separation

Acetone was removed from the reaction mixture under reduced pressure and the residue taken up in dichloromethane (50 ml) and filtered through a bed of celite, with the filter cake washed twice with dichloromethane. The combined organic filtrate was washed twice with saturated sodium bicarbonate solution and water. The washed filtrate was mixed with bentonite (10.0 g), filtered, and solvent removed by distillation to form a crude material. The crude product was dissolved in methanol by heating, and then cooled to produce 2.95 g (85.75%) of white crystalline 3β-Acetoxyandrost-5-en-7,17-dione (7-oxo-DHEAAc) having a melting point of 185–186° C.

EXAMPLE 14

(Oxidation of 3β-hydroxy-androst-5-en-17-one (DHEA) to 3β-hydroxy-androst-5-ene-7,17-dione (7-Oxo-DHEA)

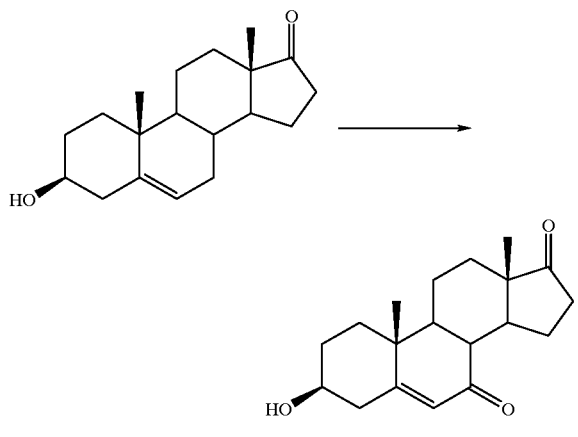

Oxidation

3β-hydroxy-androst-5-en-17-one (DHEA) (2.88 grams, 0.01 mol) and N-hydroxy phthalimide (1.8 g, 0.011 mol) were dissolved in acetone (50 ml) and water (5 ml). The mixture was stirred vigorously at room temperature and solid chromium trioxide (0.833 g, 0.00833 mol) was added. After 10 and 20 hours of continuous stirring at room temperature, an additional amount of solid chromium trioxide (0.833 g, 0.00833 mol) was added at each time interval, and the reaction mixture stirred continuously until the reaction had run to completion (48 hours).

Separation

Acetone was removed from the reaction mixture under reduced pressure and the residue taken up in dichloromethane (50 ml) and filtered through a bed of celite, with the filter cake washed twice with dichloromethane. The combined organic filtrate was washed twice with saturated sodium bicarbonate solution and water. The washed filtrate was mixed with bentonite (10.0 g), filtered, and solvent removed by distillation to form a crude material. The crude product was dissolved in methanol by heating, and cooled to produce 1.8 g (60%) of 7-oxo-DHEA having a melting point of 239–241° C.

EXAMPLE 15

Oxidation of R(+)α-Pinene to R(+)α-Verbenone

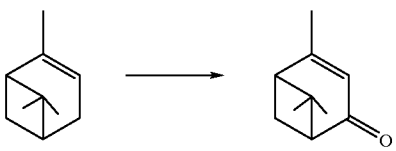

Oxidation

R(+)α-pinene (1.34 grams, 0.01 mol) and N-hydroxy phthalimide (1.8 g, 0.011 mol) were dissolved in acetone (45 ml) and water (5 ml). The mixture was stirred vigorously at room temperature and solid chromium trioxide (1.0 g, 0.01 mol) was added. After 3 hours of continuous stirring, an additional amount of solid chromium trioxide (1.0 g, 0.01 mol) was added, and the reaction mixture stirred continuously until the reaction had run to completion (20 hours).

Separation

Acetone was removed from the reaction mixture by evaporation and the residue diluted with dichloromethane and filtered through a bed of celite, with the filter cake washed with dichloromethane. The combined filtrate was washed twice with saturated sodium bicarbonate solution and water, and the solvent evaporated to form a crude product. The crude product was chromatographed on a silica gel column (70–230). The product was eluted with ethyl acetate (5% v/v) in petroleum ether to yield 0.76 g (51.35%) of pure R(+)α-verbenone.

EXAMPLE 16

Oxidation of Fluorene to Fluorenone

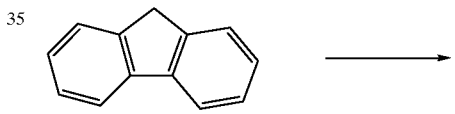

Oxidation

Fluorene (1.66 grams, 0.01 mol) and N-hydroxy phthalimide (1.8 g, 0.011 mol) were dissolved in acetone (45 ml) and water (5 ml). The mixture was stirred vigorously at room temperature and solid chromium trioxide (1.0 g, 0.001 mol) was added. After 6 and 12 hours of continuous stirring at room temperature, an additional amount of solid chromium trioxide (1.0 g, 0.001 mol) was added at each time interval, and the reaction mixture stirred continuously until the reaction had run to approximately 90% completion (24 hours).

Separation

Solvent was removed under vacuum and dichloromethane (50 ml) added to the residue. The organic layer was filtered through a bed of celite and the filter cake washed three times with dichloromethane. The combined organic filtrate was washed with water, saturated sodium bicarbonate solution, and water, and then dried. The solvent was distilled to yield crude fluorenone. The crude fluorenone was recrystallized from methanol to yield 1.2 g (74% yield based on 90% conversion) of fluorenone having a melting point of 82–84° C.

EXAMPLES 17–19

Oxidation with Pyridinium Chlorochromate and N-Hydroxy Phthalimide

EXAMPLE 17

(Oxidation of 3β-Acetoxyandrost-5-en-17-one (DHEAAc) to 3β-Acetoxyandrost-5-ene-7,17-dione (7-Oxo-DHEAAc)

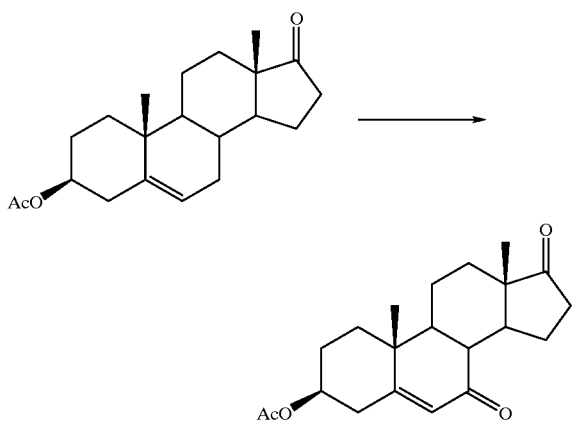

Oxidation

3β-Acetoxyandrost-5-en-17-one (DHEAAc) (3.3 g, 0.01 mol) and N-hydroxy phthalimide (1.8 g, 0.011 mol) were dissolved in acetone (45 ml) and water (5 ml). The mixture was stirred vigorously at room temperature and solid pyridinium chlorochromate (2.16 g, 0.01 mol) was added over one hour. After 10 hours of continuous stirring at room temperature, an additional amount of solid pyridinium chlorochromate (2.16 g, 0.01 mol) was added, and the reaction mixture stirred continuously until the reaction had run to completion (40 hours).

Separation

Acetone was removed from the reaction mixture under reduced pressure and the residue taken up in dichloromethane (50 ml) and then filtered through a bed of celite, with the filter cake washed twice with dichloromethane. The combined organic filtrate was washed twice with saturated sodium bicarbonate solution and water. The washed filtrate was mixed with bentonite (10.0 g), filtered, and solvent removed by distillation to form a crude material. The crude product was dissolved in methanol by heating, and cooled to produce 2.9 g (84.3%) of white crystalline 3β-Acetoxyandrost-5-en-7,17-dione (7-oxo-DHEAAc) having a melting point of 185–186° C.

EXAMPLE 18

Oxidation of R(+)α-Pinene to R(+)α-Verbenone

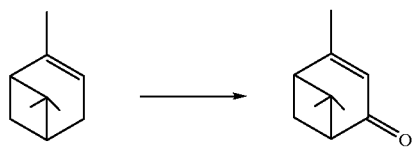

Oxidation

R(+)α-pinene (1.34 grams, 0.01 mol) and N-hydroxy phthalimide (1.8 g, 0.011mol) were dissolved in acetone (45 ml) and water (5 ml). The mixture was stirred vigorously at room temperature and solid pyridinium chlorochromate (2.16 g, 0.01 mol) was added over one hour. After 10 hours of continuous stirring, an additional amount of solid pyridinium chlorochromate (2.16 g, 0.01 mol) was added, and the reaction mixture stirred continuously until the reaction had run to completion (24 hours).

Separation

The reaction mixture was poured into water and the solution extracted with dichloromethane—petroleum ether (6:4, v/v). The extract was washed twice with saturated sodium bicarbonate solution and water, and the solvent evaporated to form a crude product.

The crude product was chromatographed on a silica gel column (70–230). The product was eluted with ethyl acetate (5% v/v) in hexane to yield 0.8 g of R(+)α-verbenone.

Yield

Total yield of purified R(+)α-verbenone (95% purity, HPLC at 254 nm) was 0.8 grams (54%).

EXAMPLE 19

Oxidation of Diphenyl Methane to Benzophenone

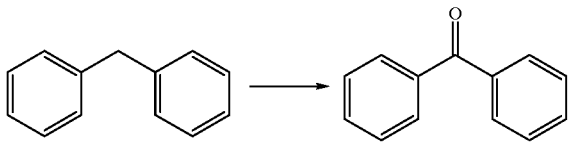

EXAMPLE 19a

Oxidation

Diphenyl methane (1.68 grams, 0.01 mol) and N-hydroxy phthalimide (1.8 g, 0.011 mol) were dissolved in acetone (45 ml) and water (5 ml). The mixture was stirred vigorously at room temperature and solid pyridinium chlorochromate (2.15 g, 0.01 mol) was added over one hour. After 10 hours of continuous stirring, an additional amount of solid pyridinium chlorochromate (2.16 g, 0.01 mol) was added, and the reaction mixture stirred continuously for 40 hours, at which time approximately 60% of the starting materials had reacted.

Separation

The reaction mixture was poured into water and the solution extracted with dichloromethane—petroleum ether (6:4, v/v). The extract was washed twice with saturated sodium bicarbonate solution and water, and the organic phase dried over magnesium sulfate and evaporated. The residue was chromatographed on a column of silica gel (70–230 mesh) and eluted with ethyl acetate (0–5% (v/v)) in petroleum ether. The fractions eluted with petroleum ether were combined and distilled to yield 0.69 g of unreacted diphenyl methane. The ethyl acetate-hexane fractions were combined and evaporated to yield benzophenone as a white oil (0.92 grams).

Yield

Total yield of benzophenone was 0.92 grams (86% based upon 59% conversion).

EXAMPLE 19b

Solvent Variation

The same oxidation reaction of diphenyl methane as set forth in Example 19a was carried out using acetonitrile and water in place of acetone and water as the reaction solvents. All other reactants and processing conditions remained the same. Again, 0.7 g of starting material was recovered and 0.92 g of benzophenone was obtained, resulting in an identical yield of 86% based on 59% conversion.

EXAMPLES 20–23

Oxidation with Pyridinium Dichromate (PCD) and N-Hydroxy Phthalimide

EXAMPLE 20

(Oxidation of 3β-Acetoxyandrost-5-en-17-one (DHEAAc) to 3β-Acetoxyandrost-5-ene-7,17-dione (7-Oxo-DHEAAc))

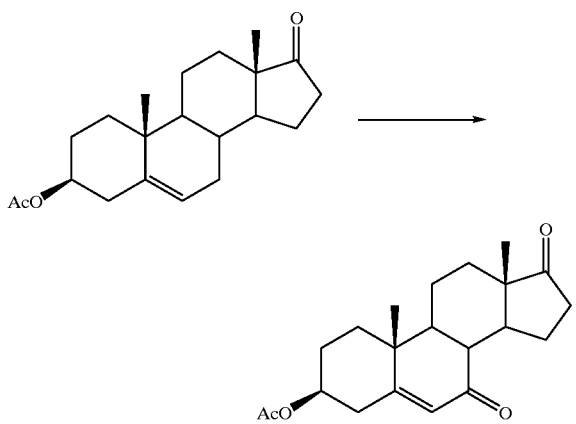

Oxidation

3β-Acetoxyandrost-5-en-17-one (DHEAAc) (0.33 g, 0.001 mol) and N-hydroxy phthalimide (0.18 g, 0.0011 mol) were dissolved in acetonitrile (9 ml) and water (1 ml). The mixture was stirred vigorously at room temperature and solid pyridinium dichromate (0.38 g, 0.001 mol) was added over one hour. After 3 hours of continuous stirring at room temperature, an additional amount of solid pyridinium dichromate (0.38 g, 0.001 mol) was added, and the reaction mixture stirred continuously until the reaction had run to completion (20 hours).

Separation

The reaction mixture was poured into water and the aqueous solution extracted with dichloromethane. The dichloromethane extract was washed with water, saturated sodium bicarbonate solution and water. The washed organic layer was treated with bentonite, filtered, and solvent removed by distillation to form a crude material. The crude product was dissolved in methanol by heating, and cooled to produce 0.29 g (84%) of white crystalline 3β-Acetoxyandrost-5-en-7,17-dione (7-oxo-DHEAAc) having a melting point of 185–186° C.

EXAMPLE 21

(Oxidation of 3β-hydroxy-androst-5-en-17-one (DHEA) to 3β-hydroxy-androst-5-ene-7,17-dione (7-Oxo-DHEA)

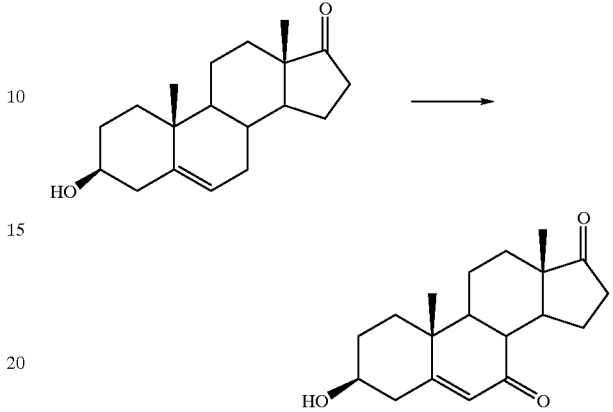

Oxidation

3β-hydroxy-androst-5-en-17-one (DHEA) (2.88 grams, 0.01 mol) and N-hydroxy phthalimide (1.8 g, 0.011 mol) were dissolved in acetonitrile (90 ml) and water (10 ml). The mixture was stirred vigorously at room temperature and solid pyridinium dichromate (3.76 g, 0.01 mol) was added. After 24 hours of continuous stirring at room temperature, an additional amount of solid pyridinium dichromate (3.76 g, 0.01 mol) was added, and the reaction mixture stirred continuously until the reaction had run to completion (48 hours).

Separation

The reaction mixture was poured into water and the aqueous solution extracted with dichloromethane. The dichloromethane extract was washed with water, saturated sodium bicarbonate solution and water. The washed filtrate was mixed with bentonite (10.0 g), filtered, and solvent removed by distillation to form a crude material. The crude product was dissolved in methanol by heating, and cooled to produce 1.7 g (56.3%) of 7-oxo-DHEA, having a melting point of 239–241° C.

EXAMPLE 22

(Oxidation of 3,17-di(ethylenedioxy)-androst-5-en-11-one to 3,17-di(ethylenedioxy)-androst-5-en-7,11-dione)

Oxidation 3,17-di(ethylenedioxy)-androst-5-en-11-one (2.27 g; 0.0058 mol) and N-hydroxy phthalimide (1.05 g, 0.0065 mol) were dissolved in acetonitrile (9 ml) and water (1 ml). The mixture was stirred vigorously at room temperature and solid pyridinium dichromate (0.22 g, 0.0058 mol) was added. The mixture was thereafter stirred vigorously until the reaction had run to completion (36 hours).

Separation

The reaction mixture was concentrated and treated with dichloromethane. The dichloromethane solution was filtered on a bed of celite and the organic layer washed with saturated sodium bicarbonate solution and water. Solvent was removed by distillation to form a crude material. The crude product was crystallized from methanol by heating to give 2.0 g (85.8%) of white crystalline 3,17-di(ethylenedioxy)-androst-5-en-7,11-dione having a melting point of 188–190° C.

EXAMPLE 23

Oxidation of 3β-Chloroandrost-5-en-17-one to 3β-Chloroandrost-5-en-7,17-dione

Oxidation

3β-Chloroandrost-5-en-17-one (0.4 g, 0.0013 mol) and N-hydroxy phthalimide (0.3 g, 0.0018 mol) were dissolved in acetone (9 ml) and water (1 ml). The mixture was stirred vigorously at room temperature and solid pyridinium dichromate (0.8 g, 0.002 mol) was added. The mixture was thereafter stirred vigorously until the reaction had run to completion (20 hours).

Separation

The reaction mixture was concentrated and treated with dichloromethane. The dichloromethane solution was filtered on a bed of celite and the organic layer washed with saturated sodium bicarbonate solution and water. Solvent was removed by distillation to form a crude material. The crude product was crystallized from methanol by heating to give 0.38 g (90.9%) of white crystalline 3β-chloro-androst-5-en-7,17-dione having a melting point of 189–191 °C.

We claim:

1. A process for effecting the allylic oxidation of an allylic compound to yield an allylic ketone or aldehyde, comprising oxidizing the allylic compound with a combination of N-hydroxy dicarboxylic acid imide and a chromium-containing oxidant.

2. The process of claim 1 wherein the allylic compound and N-hydroxy dicarboxylic acid imide are dissolved in a suitable organic solvent.

3. The process of claim 1 wherein the allylic compound is an aliphatic compound.

4. The process of claim 1 wherein the allylic compound is a benzylic compound.

5. The process of claim 1 wherein the allylic compound is a steroid.

6. The process of claim 5 wherein the steroid is an isoprenoid.

7. The process of claim 5 wherein the steroid is a Δ5 androstene.

8. The process of claim 7 wherein the Δ5 androstene is dehydroepiandrosterone.

9. The process of claim 1 wherein the N-hydroxy dicarboxylic acid imide is an N-hydroxy imide of dicarboxylic acids of the general formula:

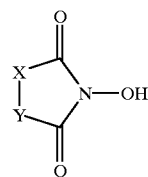

wherein X-Y is a saturated or unsaturated aliphatic hydrocarbon residue, aromatic hydrocarbon residue or a group derived from one of these groups.

10. The process of claim 1 wherein the N-hydroxy dicarboxylic acid imide is selected from the group consisting of N-hydroxy succinimide, and N-hydroxy-phthalimide, N-hydroxy imides of naphthalene dicarboxylic acids.

11. The process of claim 10 wherein the N-hydroxy dicarboxylic acid imide is N-hydroxy-phthalimide.

12. The process of claim 1 wherein the chromium containing compound is a $Cr^{3+}$, $Cr^{4+}$, $Cr^{5+}$ or $Cr^{6+}$ compound.

13. The process of claim 1 wherein the chromium-containing oxidant is selected from the group consisting of (i) sodium dichromate monohydrate, (ii) chromium trioxide, (iii) pyridinium chlorochromate, (iv) pyridinium dichromate, and (v) chromium perchlorate hexahydrate.

14. The process of claim 6 wherein the isoprenoid is oxidized by the combination of N-hydroxy dicarboxylic acid imide and chromium-containing oxidant at a temperature of between about 20 to 30° C.

15. A process for allylically oxidizing an allylic compound yielding an allylic ketone or aldehyde, comprising: dissolving an allylic compound in an organic solvent, adding an N-hydroxy dicarboxylic acid imide and a chromium-containing oxidant to the dissolved allylic compound under conditions effective for achieving allylic oxidation of the allylic compound, and separating the allylically oxidized allylic compound from the organic solvent.

16. The process of claim 15 further comprising incorporating water into the organic solvent.

17. The process of claim 16 wherein the organic solvent comprises an organic solvent system comprising a water miscible organic solvent, and about 5% to 20% (v/v) water.

18. The process of claim 15 wherein the allylic compound is a steroid.

19. The process of claim 18 wherein the steroid is dehydroepiandrosterone.

* * * * *